US006780896B2

(12) United States Patent
MacDonald et al.

(10) Patent No.: US 6,780,896 B2
(45) Date of Patent: Aug. 24, 2004

(54) STABILIZED PHOTOINITIATORS AND APPLICATIONS THEREOF

(75) Inventors: John Gavin MacDonald, Decatur, GA (US); Jason Lye, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/325,492

(22) Filed: Dec. 20, 2002

(65) Prior Publication Data

US 2004/0122124 A1 Jun. 24, 2004

(51) Int. Cl.[7] ............................ C08F 2/50; G03F 7/079; C07F 3/06
(52) U.S. Cl. ............................ 522/50; 522/51; 522/52; 522/63; 522/65; 522/66; 430/281.1; 544/106; 544/64; 546/298; 546/2; 549/13; 549/3; 556/130; 556/7; 556/118
(58) Field of Search ............................ 522/16, 18, 26, 522/28, 50, 51, 53, 63, 65, 664; 430/281.1; 544/64, 106; 546/2

(56) References Cited

U.S. PATENT DOCUMENTS

| | | | | |
|---|---|---|---|---|
| 3,794,497 A | * | 2/1974 | Pratt et al. ............... | 430/281.1 |
| 4,325,735 A | * | 4/1982 | Ohta et al. | |
| 4,336,027 A | * | 6/1982 | Tussing | |
| 4,585,484 A | * | 4/1986 | Haruta et al. | |
| 4,701,128 A | * | 10/1987 | Fitzig et al. | |
| 4,726,844 A | * | 2/1988 | Greenwood | |
| 4,767,459 A | * | 8/1988 | Greenwood et al. | |
| 4,783,220 A | * | 11/1988 | Gamble et al. | |
| 4,812,492 A | * | 3/1989 | Eckes et al. | |
| 4,836,851 A | * | 6/1989 | Pawlowski et al. | |
| 4,957,553 A | * | 9/1990 | Koike et al. | |
| 4,963,189 A | * | 10/1990 | Hindagolla | |
| 5,006,862 A | * | 4/1991 | Adamic | |
| 5,017,227 A | * | 5/1991 | Koike et al. | |
| 5,034,058 A | * | 7/1991 | Akiyama et al. | |
| 5,062,893 A | * | 11/1991 | Adamic et al. | |
| 5,064,694 A | * | 11/1991 | Gee | |
| 5,067,980 A | * | 11/1991 | Koike et al. | |
| 5,069,719 A | * | 12/1991 | Ono | |
| 5,091,004 A | * | 2/1992 | Tabayashi et al. | |
| 5,092,926 A | * | 3/1992 | Owatari | |
| 5,098,474 A | * | 3/1992 | Pawlowski et al. | |
| 5,100,470 A | * | 3/1992 | Hindagolla et al. | |
| 5,133,803 A | * | 7/1992 | Moffatt | |
| 5,145,518 A | * | 9/1992 | Winnik et al. | |
| 5,151,128 A | * | 9/1992 | Fukushima et al. | |
| 5,156,675 A | * | 10/1992 | Breton et al. | |
| 5,160,535 A | * | 11/1992 | Cooke et al. | |
| 5,190,581 A | * | 3/1993 | Fukushima et al. | |
| 5,203,912 A | * | 4/1993 | Greenwood et al. | |
| 5,220,346 A | * | 6/1993 | Carreira et al. | |
| 5,223,026 A | * | 6/1993 | Schwarz, Jr. | |
| 5,226,957 A | * | 7/1993 | Wickramanayake et al. | |
| 5,230,732 A | * | 7/1993 | You et al. | |
| 5,258,065 A | * | 11/1993 | Fujisawa | |
| 5,269,840 A | * | 12/1993 | Morris et al. | |
| 5,274,025 A | * | 12/1993 | Stockl et al. | |

(List continued on next page.)

FOREIGN PATENT DOCUMENTS

| | | |
|---|---|---|
| EP | 0972563 A1 | 1/2000 |
| WO | WO 9814524 A1 | 4/1998 |
| WO | WO 9947252 A2 | 3/1999 |
| WO | WO 9947253 A1 | 3/1999 |
| WO | WO 0003797 A1 | 1/2000 |
| WO | WO 0066090 A1 | 11/2000 |
| WO | WO 0106045 A1 | 1/2001 |
| WO | WO 0202347 A1 | 1/2002 |

OTHER PUBLICATIONS

Article–*Uniform Deposition of Ultrathin Polymer Films on the Surfaces of $Al_2O_3$ Nanoparticles by a Plasma Treatment*, Donglu Shi, S. X. Want, Jim J. van Ooji, L. M. Wang, Jiangang Zhao, and Zhou Yu, Jun. 2000, 15 pages.

Article–*Development of Novel Dye–Doped Silica Nanoparticles for Biomarker Applications*, Swadeshmukul Santra, Kemin Wang, Rovelyn Tapec, and Weihong Tan, Journal of Biomedical Optics, vol. 6, No. 2, Apr. 2001, pp. 160–166.

Article–*Nanoparticles Based on Polyelectrolyte Complexes: Effect of Structure and Net Charge on the Sorption Capability for Solved Organic Molecules*, H. M. Buchhammer, G. Petzold, and K. Lunkwitz, Colloid Polym. Sci., vol. 278, No. 9, Sep. 2000, pp. 841–847.

Article–*Industrial Organic Pigments*, W. Herbst and K. Hunger, 1997, 6 pages.

Product Information–Aldrich, 2000–2001, 4 pages.

Abstracts of Papers, 221st ACS National Meeting, San Diego, CA, Apr. 1–5, 2000.

Article–*Adsorption and Encapsulation of Fluorescent Probes in Nanoparticles*, Olga V. Makarova, Agnes E. Ostafin, Hirokazu Miyoshi, and James R. Norris, Jr., The Journal of Physical Chemistry B®, vol. 103, No. 43, Oct. 28, 1999, pp. 9080–9084.

Article–*UV Excimer Radiation from Dielectric–Barrier Discharges*, B. Eliasson and U. Kogelschatz, Applied Physics B, vol. B 46, No. 4, Aug. 1988, pp. 299–303.

Article–*Silent Discharges for the Generation of Ultraviolent and Vacuum Ultraviolent Excimer Radiation*, Ulrich Kogelschatz, Pure AND aPPLIED cHEMISTRY, VOL. 62, nO. 9, 1990, PP. 1667–1674.

*Primary Examiner*—Susan Berman
(74) *Attorney, Agent, or Firm*—Dority & Manning, P.A.

(57) ABSTRACT

Zinc-complex photoiniators and applications therefore are disclosed. The zinc-complex photoinitiators of the present invention include various pendent groups which serve to protect the compound from hydrolysis. In this manner, the stability of the photoinitiator is increased. The photoinitiators of the present invention can be used in many different processes and applications. For example, the photoinitiators are well suited for use in photocurable inks as used in ink jet printers or on a printing press.

66 Claims, No Drawings

U.S. PATENT DOCUMENTS

| | | | | |
|---|---|---|---|---|
| 5,302,195 | A | * | 4/1994 | Helbrecht et al. |
| 5,340,929 | A | * | 8/1994 | Ono et al. |
| 5,366,947 | A | * | 11/1994 | Muller et al. ............... 502/112 |
| 5,370,730 | A | * | 12/1994 | Gregory et al. |
| 5,382,283 | A | * | 1/1995 | Yui et al. |
| 5,431,723 | A | * | 7/1995 | Bermes et al. |
| 5,439,514 | A | * | 8/1995 | Kashiwazaki et al. |
| 5,441,561 | A | * | 8/1995 | Chujo et al. |
| 5,484,475 | A | * | 1/1996 | Breton et al. |
| 5,512,095 | A | * | 4/1996 | Sens et al. |
| 5,531,817 | A | * | 7/1996 | Shields et al. |
| 5,538,548 | A | * | 7/1996 | Yamazaki |
| 5,565,022 | A | * | 10/1996 | Wickramanayake |
| 5,605,566 | A | * | 2/1997 | Yui et al. |
| 5,626,654 | A | * | 5/1997 | Breton et al. |
| 5,633,109 | A | * | 5/1997 | Jennings et al. |
| 5,656,072 | A | * | 8/1997 | Kato et al. |
| 5,661,197 | A | * | 8/1997 | Villiger et al. |
| 5,667,572 | A | * | 9/1997 | Taniguchi et al. |
| 5,679,138 | A | * | 10/1997 | Bishop et al. |
| 5,679,724 | A | * | 10/1997 | Sacripante et al. |
| 5,681,380 | A | * | 10/1997 | Nohr et al. |
| 5,684,063 | A | * | 11/1997 | Patel et al. |
| 5,693,126 | A | * | 12/1997 | Ito |
| 5,725,643 | A | * | 3/1998 | Higashiyama |
| 5,749,951 | A | * | 5/1998 | Yoshiike et al. |
| 5,753,026 | A | * | 5/1998 | Kuntz et al. |
| 5,756,561 | A | * | 5/1998 | Wang et al. |
| 5,769,931 | A | * | 6/1998 | Wang et al. |
| 5,777,639 | A | * | 7/1998 | Kageyama et al. |
| 5,785,745 | A | * | 7/1998 | Lauw et al. |
| 5,788,749 | A | * | 8/1998 | Breton et al. |
| 5,788,753 | A | * | 8/1998 | Pawlowski et al. |
| 5,795,985 | A | * | 8/1998 | Husler et al. ............... 544/106 |
| 5,810,917 | A | * | 9/1998 | Yamazaki et al. |
| 5,814,685 | A | * | 9/1998 | Satake et al. |
| 5,833,744 | A | * | 11/1998 | Breton et al. |
| 5,843,509 | A | * | 12/1998 | Calvo Salve et al. |
| 5,852,073 | A | * | 12/1998 | Villiger et al. |
| 5,855,660 | A | * | 1/1999 | Bujard et al. |
| 5,868,823 | A | * | 2/1999 | Yamazaki et al. |
| 5,879,439 | A | * | 3/1999 | Nagai et al. |
| 5,880,176 | A | * | 3/1999 | Kamoto et al. |
| 5,882,391 | A | * | 3/1999 | Gregory et al. |
| 5,882,392 | A | * | 3/1999 | Gregory et al. |
| 5,888,286 | A | * | 3/1999 | Gregory et al. |
| 5,891,230 | A | * | 4/1999 | Gregory et al. |
| 5,891,232 | A | * | 4/1999 | Moffatt et al. |
| 5,891,934 | A | * | 4/1999 | Moffatt et al. |
| 5,911,816 | A | | 6/1999 | Gore |
| 5,916,596 | A | * | 6/1999 | Desai et al. |
| 5,928,416 | A | * | 7/1999 | Gundlach et al. |
| 5,928,419 | A | * | 7/1999 | Uemura et al. |
| 5,935,309 | A | * | 8/1999 | Moffatt et al. |
| 5,935,310 | A | * | 8/1999 | Engel et al. |
| 5,942,027 | A | * | 8/1999 | Ikai et al. |
| 5,944,883 | A | * | 8/1999 | Saibara et al. |
| 5,948,155 | A | * | 9/1999 | Yui et al. |
| 5,955,515 | A | | 9/1999 | Kimura et al. |
| 5,958,998 | A | | 9/1999 | Foucher et al. |
| 5,962,566 | A | | 10/1999 | Grandfils et al. |
| 5,964,926 | A | | 10/1999 | Cohen |
| 5,968,244 | A | | 10/1999 | Ueda et al. |
| 5,972,389 | A | | 10/1999 | Shell et al. |
| 5,973,025 | A | | 10/1999 | Nigam et al. |
| 5,973,027 | A | | 10/1999 | Howald et al. |
| 5,980,623 | A | | 11/1999 | Hiraoka et al. |
| 5,981,623 | A | | 11/1999 | McCain et al. |
| 5,993,527 | A | | 11/1999 | Tochihara et al. |
| 5,993,856 | A | | 11/1999 | Ragavan et al. |
| 6,015,454 | A | | 1/2000 | Lacroix et al. |
| 6,015,455 | A | | 1/2000 | Yano et al. |
| 6,019,827 | A | | 2/2000 | Wickramanayake et al. |
| 6,024,785 | A | | 2/2000 | Morimoto |
| 6,024,786 | A | | 2/2000 | Gore |
| 6,025,412 | A | | 2/2000 | Sacripante et al. |
| 6,033,463 | A | | 3/2000 | Yui et al. |
| 6,034,154 | A | | 3/2000 | Kase et al. |
| 6,037,391 | A | | 3/2000 | Iida |
| 6,045,606 | A | | 4/2000 | Matzinger |
| 6,048,390 | A | | 4/2000 | Yano et al. |
| 6,051,057 | A | | 4/2000 | Yatake et al. |
| 6,090,193 | A | | 7/2000 | Nigam et al. |
| 6,099,627 | A | | 8/2000 | Saibara et al. |
| 6,110,266 | A | | 8/2000 | Gonzalez-Blanco et al. |
| 6,113,680 | A | | 9/2000 | Aoyama et al. |
| 6,121,365 | A | | 9/2000 | Saibara et al. |
| 6,129,786 | A | | 10/2000 | Camara et al. |
| 6,140,390 | A | | 10/2000 | Bugner et al. |
| 6,147,139 | A | | 11/2000 | Shaw-Klein et al. |
| 6,149,719 | A | | 11/2000 | Houle |
| 6,153,001 | A | | 11/2000 | Suzuki et al. |
| 6,156,649 | A | | 12/2000 | Hause et al. |
| 6,165,440 | A | | 12/2000 | Esenaliev |
| 6,171,382 | B1 | | 1/2001 | Stubbe et al. |
| 6,486,227 | B2 | | 11/2002 | Nohr et al. |

* cited by examiner

STABILIZED PHOTOINITIATORS AND APPLICATIONS THEREOF

BACKGROUND OF THE INVENTION

Polymers have served essential needs in society. For many years, these needs were filled by natural polymers. More recently, synthetic polymers have played an increasingly greater role, particularly since the beginning of the 20th century. Especially useful polymers are those prepared by an addition polymerization mechanism, i.e., free radical chain polymerization of unsaturated monomers, and include, by way of example only, coatings and adhesives. In fact, the majority of commercially significant processes are based on free-radical chemistry. That is, chain polymerization is initiated by a reactive species, which often is a free radical. The source of the free radicals is termed an initiator or photoinitiator.

Improvements in free radical chain polymerization have focused both on (1) more reactive monomer and pre-polymer materials and (2) the photoinitiator. Whether a particular unsaturated monomer can be converted to a polymer requires structural, thermodynamic, and kinetic feasibility. Even when all three exist, kinetic feasibility is achieved in many cases only with a specific type of photoinitiator. Moreover, the photoinitiator can have a significant effect on reaction rate which, in turn, may determine the commercial success or failure of a particular polymerization process or product.

A free radical-generating photoinitiator may generate free radicals in several different ways. For example, the thermal, homolytic dissociation of an initiator typically directly yields two free radicals per initiator molecule. A photoinitiator, i.e., an initiator which absorbs light energy, may produce free radicals by one of three pathways:

(1) the photoinitiator undergoes excitation by energy absorption with subsequent decomposition into one or more radicals;

(2) the photoinitiator undergoes excitation and the excited species interacts with a second compound (by either energy transfer or a redox reaction) to form free radicals from the latter and/or former compound(s); or (3) the photoinitiator undergoes an electron transfer to produce a radical cation and a radical anion.

While any free radical chain polymerization process should avoid the presence of species which may prematurely terminate the polymerization reaction, prior photoinitiators present special problems. For example, absorption of the light by the reaction medium may limit the amount of energy available for absorption by the photoinitiator. Also, the often competitive and complex kinetics involved may have an adverse effect on the reaction rate. Moreover, some commercially available radiation sources, such as medium and high-pressure mercury and xenon lamps, may emit over a wide wavelength range, thus producing individual emission bands of relatively low intensity. Many photoinitiators only absorb over a small portion of the emission spectra and, as a consequence, much of the lamps' radiation remains unused. In addition, most known photoinitiators have only moderate "quantum yields" (generally less than 0.4) at these wavelengths, indicating that the conversion of light radiation to radical formation can be more efficient.

Many commercially available photoinitiators, including IRGACURE® 369, are presently used in ink compositions to accelerate ink drying in "radiation-drying printing." As used herein, the term "radiation-drying printing" refers to any printing method which utilizes radiation as a drying means. Radiation-drying printing includes, for example, offset printing operations, such as on a Heidelberg press, flexographic printing, and flatbed printing. Commercially available photoinitiator systems have a number of shortcomings. First, most of the commercially available photoinitiator systems require a relatively large amount of photoinitiator in the ink composition to fully cureldry the ink composition. This leads to undesirable extractables within the ink composition. Second, most of the commercially available photoinitiator systems require a high-energy radiation source to induce photocuring. Moreover, even with the high-energy radiation source, often the cure results are unsatisfactory. Third, many commercially available photoinitiator systems are highly reactive to oxygen and must be used under a nitrogen blanket. Fourth, even with a large amount of photoinitiator and a high energy light source, the commercially available photoinitiator systems require a dry/cure time only accomplished by multiple passes, as many as 15 passes, under a light source, which significantly limits the output of a radiation-drying printing press.

In view of the above drawbacks of the prior art, a new class of energy-efficient photoinitiators were developed which are disclosed in U.S. Pat. No. 6,486,227 to Nohr et al., which is incorporated herein by reference in its entirety. In Nohr et al., zinc-complex photoinitiators are disclosed. The photoinitiators may be cured in air as well as a nitrogen atmosphere. Further, the photoinitiators disclosed in Nohr et al. have excellent photoreactivity characteristics making them well suited for use in the radiation-drying printing industry.

Indeed, the photoinitiators disclosed in U.S. Pat. No. 6,486,227 represent advances in the art of photoinitiators. The present invention is directed to further improvements in the same class of photoinitiators disclosed in Nohr et al. In particular, the present invention is directed to further improving the stability of zinc-complex photoinitiators.

SUMMARY OF THE INVENTION

The present invention is generally directed to zinc-complex photoinitiators that have improved stability in some applications. In one embodiment, the photoinitiators of the present invention have the following general formula:

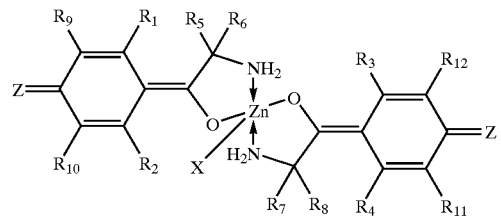

wherein Z each independently represents

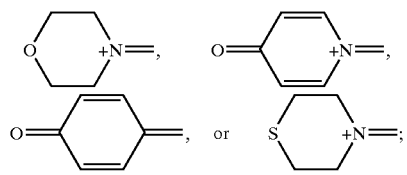

wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$ and $R_{12}$ comprise an alkyl group, an aryl group, a halo group, an alkoxy group or hydrogen and wherein at least one of $R_9$, $R_{10}$, $R_{11}$ and $R_{12}$ comprises an alkyl, an aryl, a halo, or an alkoxy group.

For many applications, at least one of $R_9$ or $R_{10}$ and at least one of $R_{11}$ or $R_{12}$ above comprise an alkyl, an aryl, a halo, or an alkoxy group. By selecting particular "R" groups, photoinitiators are produced having a desired absorption maximum, which substantially corresponds to an emission band of a radiation source and selectively varies from less than about 290 nm to greater than about 350 nm. It has also been discovered that selecting particular "R" groups can further serve to increase the stability of the photoinitiators.

In another embodiment of the present invention, the photoinitiators of the present invention can have the following formula:

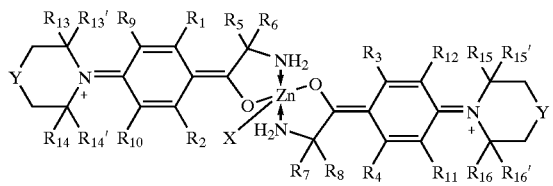

wherein Y independently represents O, S, or O=C; wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$, $R_{12}$, $R_{13}$, $R_{13}'$, $R_{14}$, $R_{14}'$, $R_{15}$, $R_{15}'$, $R_{16}$, and $R_{16}'$ comprise an alkyl group, an aryl group, a halo group, an alkoxy group, or hydrogen; $R_{13}'$ $R_{14}'$ $R_{15}'$ and $R_{16}'$ being the same or different from $R_{13}$, $R_{14}$, $R_{15}$ and $R_{16}$; and wherein at least one of $R_{13}$, $R_{14}$, $R_{15}$ and $R_{16}$ comprises an alkyl, an aryl, a halo, or an alkoxy group.

In the above photoinitiator, for many applications, at least one of $R_{13}$ or $R_{14}$ and at least one of $R_{15}$ or $R_{16}$ comprises an alkyl, an aryl, a halo, or an alkoxy group. In this embodiment, at least one of $R_9$ or $R_{10}$ and at least one of $R_{11}$ or $R_{12}$ may also comprise an alkyl, an aryl, a halo, or an alkoxy group.

The present invention is directed to the above-described photoinitiators, compositions containing the same, and methods for generating a reactive species which includes providing one or more of the photoinitiators and irradiating the one or more photoinitiators. One of the main advantages of the photoinitiators of the present invention is that they efficiently generate one or more reactive species under extremely low energy lamps, such as excimer lamps and mercury lamps, as compared to prior art photoinitiators. The photoinitiators of the present invention also efficiently generate one or more reactive species in air or in a nitrogen atmosphere. Unlike many prior photoinitiators, the photoinitiators of the present invention are not sensitive to oxygen.

The present invention is further directed to a method of efficiently generating a reactive species by matching a photoinitiator having an absorption maximum to an emission band of a radiation source, which corresponds to the absorption maximum. By adjusting the substituents of the photoinitiator, one can shift the absorption maximum of the photoinitiator from less than about 290 nm to greater than about 350 nm.

The present invention is also directed to methods of using the above-described photoinitiators to polymerize and/or photocure a polymerizable material. The photoinitiators of the present invention result in rapid curing times in comparison to the curing times of prior art photoinitiators, even with relatively low output lamps. The present invention includes a method of polymerizing a polymerizable material by exposing the polymerizable material to radiation in the presence of the efficacious wavelength specific photoinitiator composition described above. When an unsaturated oligomerimonomer mixture is employed, curing is accomplished.

The present invention further includes a film and a method for producing a film, by drawing an admixture of polymerizable material and one or more photoinitiators of the present invention, into a film and irradiating the film with an amount of radiation sufficient to polymerize the composition. The admixture may be drawn into a film on a nonwoven web or on a fiber, thereby providing a polymer-coated nonwoven web or fiber, and a method for producing the same.

The present invention is also directed to an adhesive composition comprising a polymerizable material admixed with one or more photoinitiators of the present invention. Similarly, the present invention includes a laminated structure comprising at least two layers bonded together with the above-described adhesive composition, in which at least one layer is a nonwoven web or film. Accordingly, the present invention provides a method of laminating a structure wherein a structure having at least two layers with the abovedescribed adhesive composition between the layers is irradiated to polymerize the adhesive composition.

The present invention is further directed to a method of printing, wherein the method comprises incorporating one or more photoinitiators of the present invention into an ink composition; printing the ink onto a substrate; and drying the ink with a source of radiation.

These and other features and advantages of the present invention will become apparent after a review of the following detailed description of the disclosed embodiments and the appended claims.

DETAILED DESCRIPTION

The present invention is directed to energy-efficient, reactive, photoinitiators and methods for utilizing the same. More particularly, the present invention is directed to zinc-complex photoinitiators having increased stability.

The present invention is further directed to a method of efficiently generating a reactive species by matching a photoinitiator having an absorption maximum to an emission band of a radiation source, which corresponds to the absorption maximum. The present invention also includes a method of polymerizing a polymerizable material by exposing the polymerizable material to electromagnetic radiation in the presence of one or more of the photoinitiators described above. Further, the present invention is directed to a film and a method for producing a film, by drawing an admixture of polymerizable material and one or more of the photoinitiators described above, into a film and irradiating the film with an amount of electromagnetic radiation sufficient to polymerize the admixture.

The present invention is further directed to an adhesive composition comprising a polymerizable material admixed and one or more photoinitiators of the present invention. Similarly, the present invention includes a laminated structure comprising at least two layers bonded together with the above-described adhesive composition. The present invention further provides a method of laminating a structure wherein a structure having at least two layers with the above-described adhesive composition between the layers is irradiated with appropriate electromagnetic radiation to polymerize the adhesive composition.

Definitions

As used herein, the term "reactive species" is used herein to mean any chemically reactive species including, but not limited to, free-radical, cations, anions, nitrenes, and carbenes. Illustrated below are examples of several of such species. Examples of carbenes include, for example, methylene or carbene, dichlorocarbene, diphenylcarbene, alkylcarbonyl-carbenes, siloxycarbenes, and dicarbenes. Examples of nitrenes include, also by way of example, nitrene, alkyl nitrenes, and aryl nitrenes. Cations (sometimes referred to as carbocations or carbonium ions) include, by way of illustration, a proton; primary, secondary, and tertiary alkyl carbocatons, such as methyl cation, ethyl cation, propyl cation, t-butyl cation, t-pentyl cation, t-hexyl cation; allylic cations; benzylic cations; aryl cations, such as triphenyl cation; cyclopropylmethyl cations; methoxymethyl cation; triarylsulphonium cations; and acyl cations. Cations also include those formed from various metal salts, such as tetra-n-butylammonium tetrahaloaurate(III) salts; sodium tetrachloroaurate(III); vanadium tetrachloride; and silver, copper(I) and (II), and thallium(I) triflates. Examples of anions (sometimes referred to as carbanions) include, by way of example, alkyl anions, such as ethyl anion, n-propyl anion, isobutyl anion, and neopentyl anion; cycloalkyl anions, such as cyclopropyl anion, cyclobutyl anion, and cyclopentyl anion; allylic anions; benzylic anions; aryl cations; and sulfur- or phosphorus-containing alkyl anions. Finally, examples of organometallic photoinitiators include titanocenes, fluorinated diarylitanocenes, iron arene complexes, manganese decacarbonyl, and methylcyclopentadienyl manganese tricarbonyl. Organometallic photoinitiators generally produce free radicals or cations.

As used herein, the term "quantum yield" is used herein to indicate the efficiency of a photochemical process. More particularly quantum yield is a measure of the probability that a particular molecule will absorb a quantum of light during its interaction with a photon. The term expresses the number of photochemical events per photon absorbed. Thus, quantum yields may vary from zero (no absorption) to 1.

As used herein, the term "polymerization" is used herein to mean the combining, e.g. covalent bonding, of a number of smaller molecules, such as monomers, to form large molecules, i.e., macromolecules or polymers. The monomers may be combined to form only linear macromolecules or they may be combined to form three-dimensional macromolecules, commonly referred to as crosslinked polymers.

As used herein, the term "curing" means the polymerization of functional oligomers and monomers, or even polymers, into a crosslinked polymer network. Thus, curing is the polymerization of unsaturated monomers or oligomers in the presence of crosslinking agents.

As used herein, the terms "unsaturated monomer," "functional oligomer," and "crosslinking agent" are used herein with their usual meanings and are well understood by those having ordinary skill in the art. The singular form of each is intended to include both the singular and the plural, i.e., one or more of each respective material.

As used herein, the term "unsaturated polymerizable material" is meant to include any unsaturated material capable of undergoing polymerization. The term encompasses unsaturated monomers, oligomers, and crosslinking agents. Again, the singular form of the term is intended to include both the singular and the plural.

As used herein, the term "fiber" as used herein denotes a threadlike structure. The fibers used in the present invention may be any fibers known in the art. It is to be understood that any fibers known in the art may be used in the present invention.

Photoinitiators

In U.S. Pat. No. 6,486,227 to Nohr et al., zinc-complex photoinitiators were described having the following general formula:

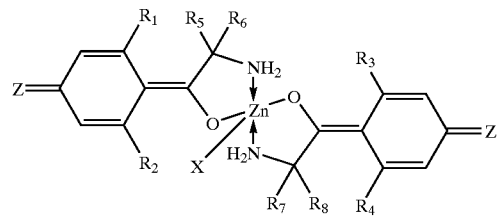

wherein Z each independently represents

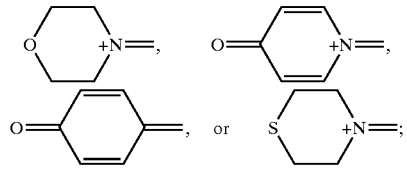

wherein $R_1$, $R_2$, $R_3$ and $R_4$ each independently represent hydrogen, an alkyl group having from one to six carbon atoms, an alkoxy group having from one to six carbon atoms, or a halogen-substtuted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$; and wherein $R_{17}$ represents H or an alkyl group having from one to eight carbon atoms.

Photoinitiators having the above formula from Nohr et al. include, but are not limited to, the following photoinitiators:

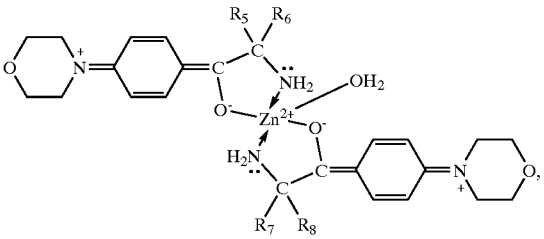

7

-continued

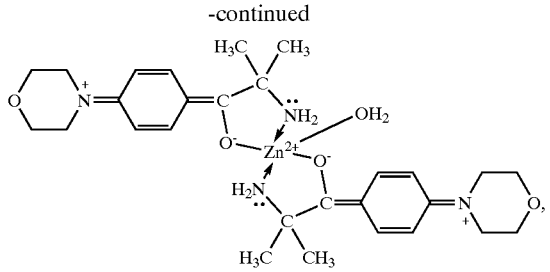

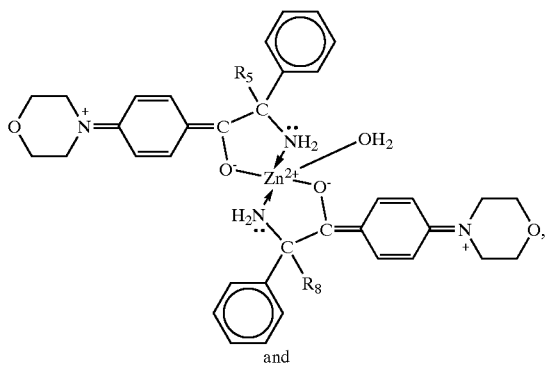
and

8

-continued

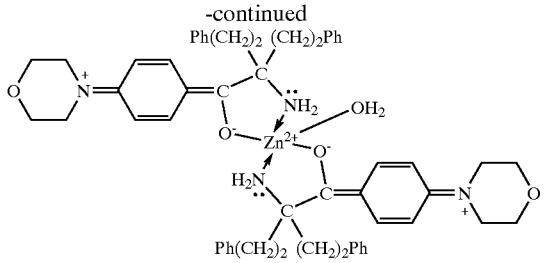

wherein $R_5$, $R_6$, $R_7$, and $R_8$ are as described above.

The above photoinitiators disclosed in Nohr et al. have shown significant improvements over commercially available photoinitiators in terms of cure speed and oxygen sensitivity. Under some circumstances, however, the above photoinitiators may show some susceptibility to hydrolysis. In particular, under some circumstances, when used in printing inks, the photoinitiators may have to be dispersed into an ink immediately prior to use to prevent degradation.

In particular, it has been realized that the structures disclosed in Nohr et al., under some circumstances, may be attacked by water at the imino moiety, leading to hydrolysis. Without wishing to be bound by theory, hydrolysis may occur as follows (X may be considered $H_2O$ in the following reactions):

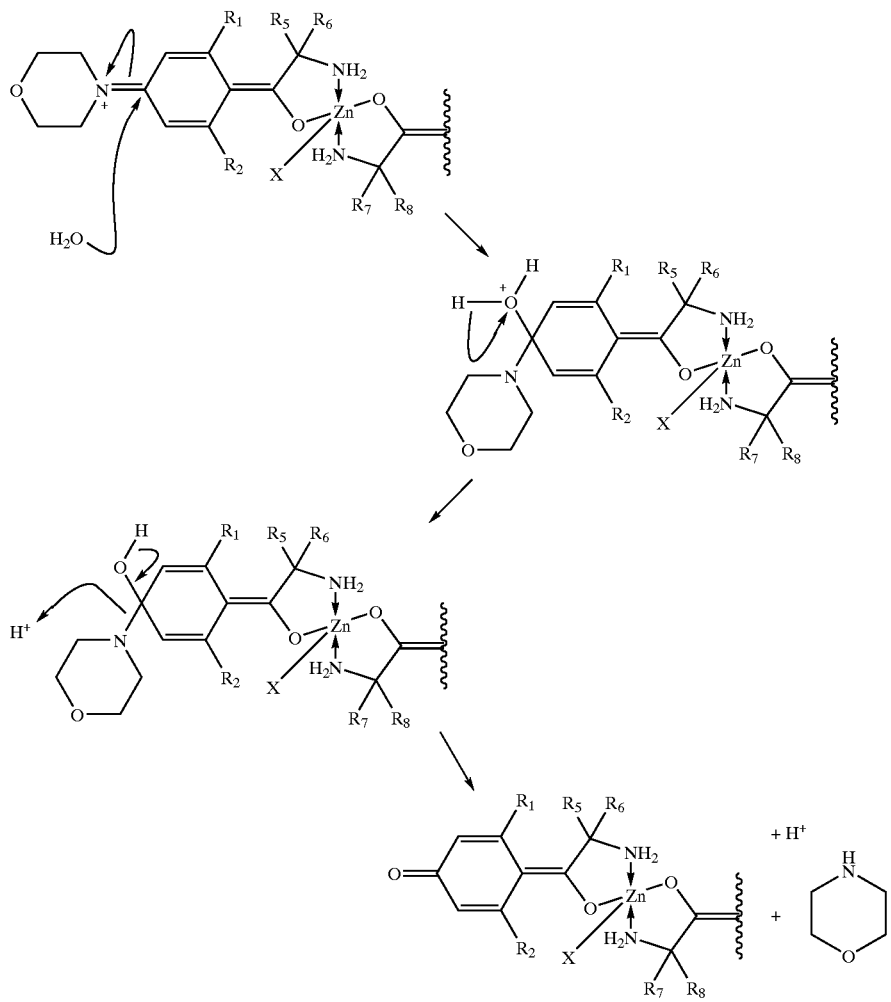

Further reactions may also occur with loss of bonding to the central metal atom as aromaticity is restored, which is shown as follows:

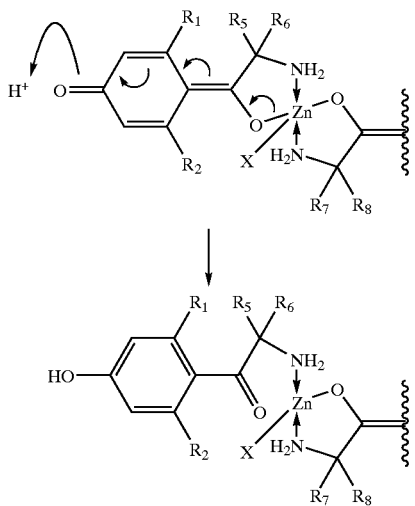

In view of the above possibilities, the present invention is directed to further improvements in the photoinitiators disclosed in Nohr et al. Specifically, the photoinitiators of the present invention include alternative substitution patterns on the zinc-complex photoinitiators that may reduce the extent of hydrolysis and thereby improve the shelf life of the compounds. For example, in one embodiment, the photoinitiators of the present invention can be represented as follows:

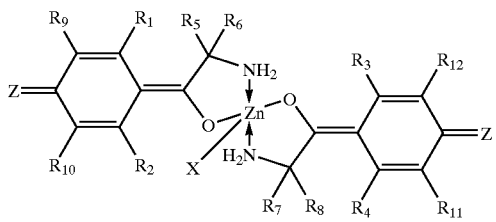

wherein Z each independently represents

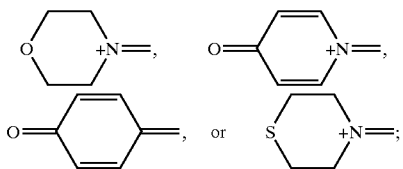

wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$ and $R_{12}$ comprise an alkyl group, an aryl group, a halo group, an alkoxy group or hydrogen and wherein at least one of $R_9$, $R_{10}$, $R_{11}$ and $R_{12}$ comprises an alkyl, an aryl, a halo, or an alkoxy group.

For many applications, at least one of $R_9$ or $R_{10}$ and at least one of $R_{11}$ or $R_{12}$ above comprises an alkyl, an aryl, a halo, or an alkoxy group. Halo groups that may be used in the present invention include a chloro group, such as chloride.

It is believed that inclusion of the $R_9$, $R_{10}$, $R_{11}$ and $R_{12}$ groups in the above compound may retard and inhibit hydrolytic attack. In particular, it is believed that the additional groups may serve to shield the compound from water molecules.

As shown by the above formula, many different photoinibators can be made according to the present invention. In one particular embodiment, the photoinitiator may have the following structure:

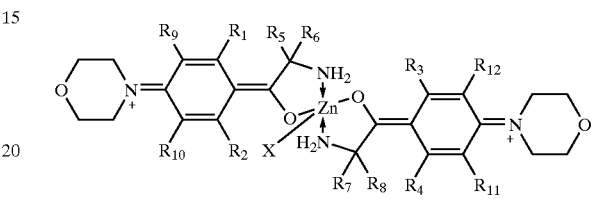

wherein the R groups and the X group are as defined above.

For many applications, $R_1$, $R_2$, $R_3$ and $R_4$ above are hydrogen. In this embodiment, $R_5$, $R_6$, $R_7$ and $R_8$ may be $CH_3$ or, alternatively, $Ph(CH_2)_2$. In another alternative structure, $R_6$ and $R_7$ may be aryl groups.

In another alternative embodiment of the present invention, the photoinitiator can be represented as follows:

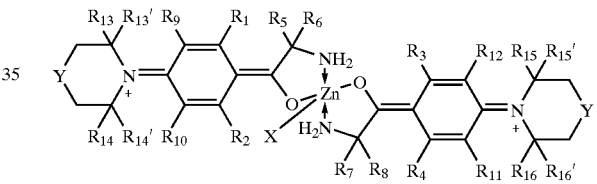

wherein Y independently represents O, S or O=C; wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$, $R_{12}$, $R_{13}$, $R_{13}'$, $R_{14}$, $R_{14}'$, $R_{15}$, $R_{15}'$, $R_{16}$, and $R_{16}'$ comprise an alkyl group, an aryl group, a halo group, an alkoxy group, or hydrogen; $R_{13}'$ $R_{14}'$ $R_{15}'$ and $R_{16}'$ being the same or different from $R_{13}$, $R_{14}$, $R_{15}$ and $R_{16}$; and wherein at least one of $R_{13}$, $R_{14}$, $R_{15}$ and $R_{16}$ comprises an alkyl, an aryl, a halo, or an alkoxy group.

As shown above, in this embodiment, the photoinitiator further includes groups $R_{13}$ through $R_{16}$ and $R_{13}'$ through $R_{16}'$. These groups can be added in addition to $R_9$ through $R_{12}$ or can be added in lieu of the $R_9$ to $R_{12}$ groups.

For many applications, at least one of $R_{13}$ or $R_{14}$ and at least one of $R_{15}$ or $R_{16}$ comprises an alkyl, an aryl, a halo, or an alkoxy group. At least one of $R_9$ or $R_{10}$ and at least one of $R_{11}$ or $R_{12}$ may also comprise one of the above groups in this embodiment.

The above photoinitiator can also be associated with one or more anions (A⁻) as shown below.

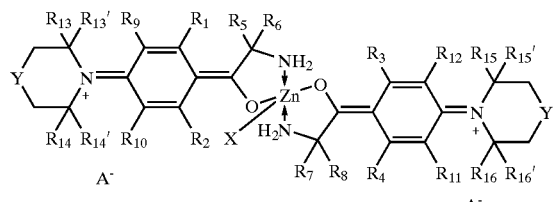

When Y is O, the above chemical structure can be represented as follows:

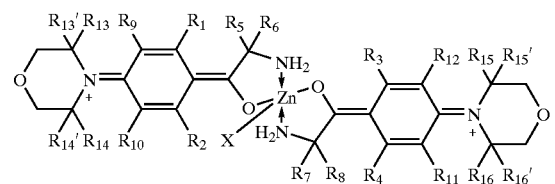

wherein the R groups and the X groups are as defined above.

The photoinitiators of the present invention may be associated with a variety of counterions. Suitable counterions possess a negative charge distribution, which is spread over a large anion, resulting in a diffused charge rather than a point charge. Examples of suitable counterions include, but are not limited to, tetraphenylboron, tetrachloroboron, tetrafluoroboron, hexafluorophosphate, and perchlorate. Desirably, the counterion comprises tetraphenylboron or tetrafluoroboron. More desirably, the counterion comprises tetrafluoroboron.

The above-described photoinitiators of the present invention may be produced by the following reaction mechanism, shown for when Z is $NC_4H_4O$ and for the embodiments above including $R_9$ through $R_{12}$.

wherein one or more compounds react with the Zn-containing compound or complex to produce a photoinitiator of the present invention and one or more anions (A⁻). Suitable Zn-containing compounds or complexes include, but are not limited to, $Zn(OEt_2)_2Cl_2$, $Zn(H_2O)_6(BF_4)_2$, and $Zn(H_2O)_6(BPh_4)_2$. In the above mechanism, the use of a particular Zn-containing compound or complex results in a particular X group and anions as shown in the table below:

| Zn-containing Compound or Complex | Resulting X Group | Resulting Anions |
|---|---|---|
| $Zn(OEt_2)Cl_2$ | $OEt_2$ | $Cl^-$ |
| $Zn(H_2O)_6(BF_4)_2$ | $H_2O$ | $BF_4^-$ |
| $Zn(H_2O)_6(BPh_4)_2$ | $H_2O$ | $BPh_4^-$ |

It should be understood that the above examples of suitable photoinitiators are only a few of the possible photoinitiators encompassed by the present invention. Any combination of photoinitiator having selected "R" groups and any of the above-mentioned counterions may be used in combination to form a photoinitiator system of the present invention. Further, the above reaction mechanism is only one example of many possible reaction mechanisms, which may include a variety of reactants, resulting in the photoinitiators of the present invention The resulting photoinitiators are relatively stable at room temperature (from about 15° C. to 25° C.) and normal room humidity (from about 5% to 60%; desirably from 5% to 30%). However, upon exposure to radiation at an appropriate wavelength, the photoinitiators efficiently produce one or more reactive species. The photoinitiators of the present invention have a high intensity of absorption. For example, the photoinitiators of the present invention have a molar extinction coefficient (absorptivity) greater than about 20,000 1 mole⁻¹ cm⁻¹. As a further example, the photoinitiators of the present invention have a molar extinction coefficient greater than about 25,000 1 mole⁻¹ cm⁻¹.

Method of Generating a Reactive Species and Applications Therefore

The present invention is further directed to a method of generating a reactive species. The method of generating a

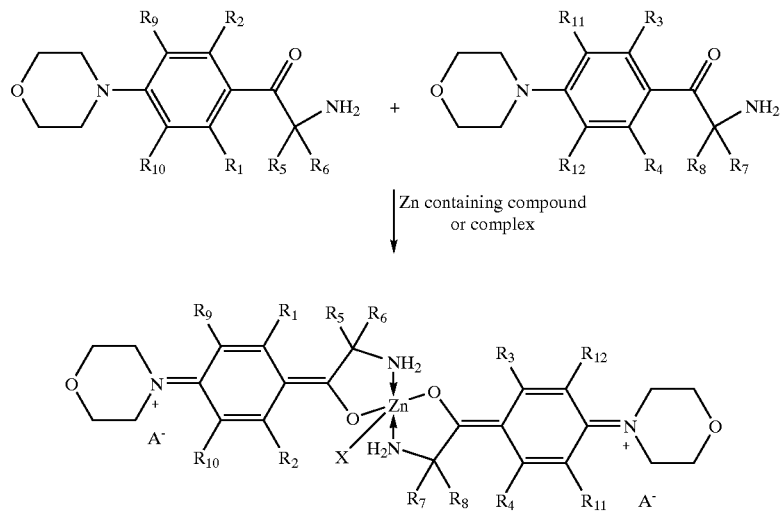

reactive species involves generating a reactive species by exposing one or more of the abovedescribed photoinitiators to radiation. The exposure of the photoinitiators to a radiation source triggers a photochemical process. As stated above, the term "quantum yield" is used herein to indicate the efficiency of a photochemical process. More particularly, quantum yield is a measure of the probability that a particular molecule (photoinitiator) will absorb a quantum of light during its interaction with a photon. The term expresses the number of photochemical events per photon absorbed. Thus, quantum yields may vary from zero (no absorption) to 1.

The photoinitiators of the present invention absorb photons having a relatively specific wavelength and transfers the absorbed energy to one or more excitable portions of the molecule. The excitable portion of the molecule absorbs enough energy to cause a bond breakage, which generates one or more reactive species. The efficiency with which a reactive species is generated with the photoinitiators of the present invention is significantly greater than that experienced with photoinitiators of the prior art as indicated by faster cure times. For example, the photoinitiators of the present invention desirably will have a quantum yield greater than about 0.8. More desirably, the quantum yield of the photoinitiators of the present invention will be greater than about 0.9. Even more desirably, the quantum yield of the photoinitiators of the present invention will be greater than about 0.95. Still more desirably, the quantum yield of the photoinitiators of the present invention will be greater than about 0.99, with the most desirable quantum yield being about 1.0.

In one embodiment of the present invention, the photoinitiators of the present invention are exposed to radiation at a desired wavelength, resulting in the generation of one or more reactive species, wherein an electron-donating solvent is used to generate one or more reactive species. Any solvent capable of donating an electron to the photoinitiators of the present invention may be used to generate one or more reactive species. Suitable electron-donating solvents include, but are not limited to, acrylates, methacylates, vinyl esters, enamines, and a combination thereof. Desirably, the electron-donating solvent comprises acrylic acid.

It is believed that the interaction between the photoinitiator of the present invention and the electron-donating solvent takes place as shown by the following reaction mechanism:

Donation of electron

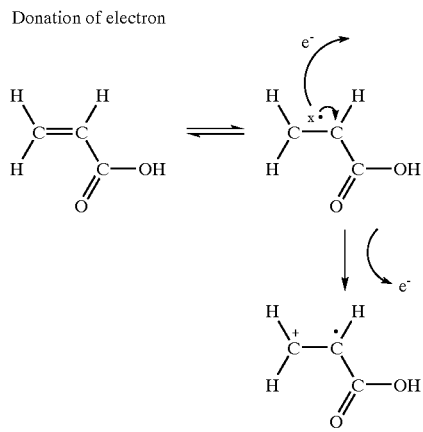

As shown above, donation of an electron from the electron-donating solvent generates a cationic free radical.

Electron Interaction With Photoinitiator:

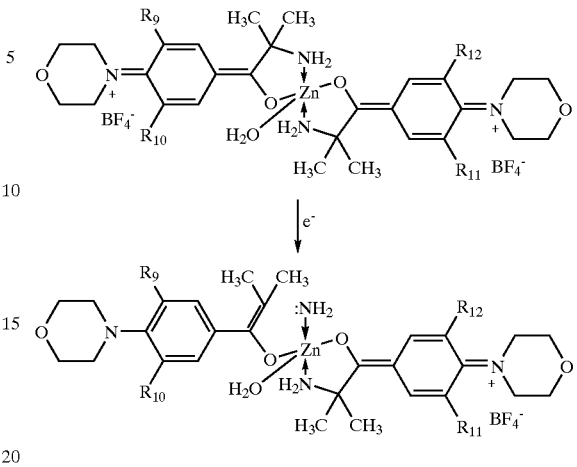

The introduction of the electron into the structure of the photoinitiator results in the formation of a carbon carbon double bond and cleavage of the carbon-nitrogen bond. The end result is a nitrogen-containing free radical.

The above mechanism generates a combination of free radicals, one of which is a cationic free radical and one of which is nitrogen radical species. In conventional electron transfer systems, an initiator generates a radical cation, which starts the polymerization process, and a radical anion, which is a chain terminator (i.e., stops polymerization). However, the method of generating a reactive species of the present invention generates a radical cation and a nitrogen radical species, both of which start the polymerization process, and neither of which act as a chain terminator (i.e., stop polymerization).

Exposing the photoinitiators of the present invention to radiation results in the generation of one or more reactive species as discussed above. Thus, the photoinitiators may be employed in any situation where reactive species are required, such as for the polymerization of an unsaturated monomer and the curing of an unsaturated oligomer/monomer mixture. The unsaturated monomers and oligomers may be any of those known to one having ordinary skill in the art. In addition, the polymerization and curing media also may contain other materials as desired, such as pigments, extenders, amine synergists, and such other additives as are well known to those having ordinary skill in the art.

By way of illustration only, examples of unsaturated monomers and oligomers include ethylene, propylene, vinyl chloride, isobutylene, styrene, isoprene, acrylonitrile, acrylic acid, methacrylic acid, ethyl acrylate, methyl methacrylate, vinyl acrylate, allyl methacrylate, tripropylene glycol diacrylate, trimethylol propane ethoxylate acrylate, epoxy acrylates, such as the reaction product of a bisphenol A epoxide with acrylic acid; polyether acrylates, such as the reaction product of acrylic acid with an adipic acid/hexanediol-based polyether, urethane acrylates, such as the reaction product of hydroxypropyl acrylate with diphenylmethane-4,4'-diisocyanate, and polybutadiene diacrylate oligomer.

The types of reactions that various reactive species enter into include, but are not limited to, addition reactions, including polymerization reactions; abstraction reactions; rearrangement reactions; elimination reactions, including decarboxylation reactions; oxidation-reduction (redox) reactions; substitution reactions; and conjugation/deconjugation reactions.

Accordingly, the present invention also comprehends a method of polymerizing a polymerizable material, such as an unsaturated monomer or epoxy compound, by exposing the polymerizable material to radiation in the presence of the effacious photoinitiators of the present invention described herein. When an unsaturated oligomerimonomer mixture is employed in place of an unsaturated monomer, curing is accomplished. It is to be understood that the polymerizable material admixed with the photoinitiators of the present invention is to be admixed by means known in the art, and that the mixture will be irradiated with an amount of radiation sufficient to polymerize the material. The amount of radiation sufficient to polymerize the material is readily determinable by one of ordinary skill in the art, and depends upon the identity and amount of photoinitiators, the identity and amount of the polymerizable material, the intensity and wavelength of the radiation, and the duration of exposure to the radiation.

Polymer Films, Coated Fibers and Webs, and Adhesive Compositions

The present invention further includes a film and a method for producing a film, by drawing an admixture of a polymerizable material and one or more photoinitiators of the present invention, into a film and irradiating the film with an amount of radiation sufficient to polymerize the composition. When the polymerizable material is an unsaturated oligomer/monomer mixture, curing is accomplished. Any film thickness may be produced, as per the thickness of the admixture formed, so long as the admixture sufficiently polymerizes upon exposure to radiation. The admixture may be drawn into a film on a nonwoven web or on a fiber, thereby providing a polymer-coated nonwoven web or fiber, and a method for producing the same. Any method known in the art of drawing the admixture into a film may be used in the present invention. The amount of radiation sufficient to polymerize the material is readily determinable by one of ordinary skill in the art, and depends upon the identity and amount of photoinitiator, the identity and amount of the polymerizable material, the thickness of the admixture, the intensity and wavelength of the radiation, and duration of exposure to the radiation.

The present invention is further directed to coatings comprising a polymerizable material admixed with one or more photoinitiators of the present invention. The coatings may be applied to a substrate and then exposed to an amount of radiation sufficient to polymerize the polymerizable material of the coating. Any substrate may be used in the practice of the present invention. Particular applications of interest include, but are not limited to, coatings on textiles, coatings on fabrics, coatings on textile fibers, and coatings on optical fibers.

The present invention also includes an adhesive composition comprising a polymerizable material admixed with one or more photoinitiators of the present invention. Similarly, the present invention includes a laminated structure comprising at least two layers bonded together with the above-described adhesive composition. In one embodiment of the present invention, a laminate is produced wherein at least one layer is a cellulosic or polyolefin nonwoven web or film. Accordingly, the present invention provides a method of laminating a structure wherein a structure having at least two layers with the above-described adhesive composition between the layers is irradiated to polymerize the adhesive composition. When the unsaturated polymerizable material in the adhesive is an unsaturated oligomer/monomer mixture, the adhesive is irradiated to cure the composition.

It is to be understood that any layers may be used in the laminates of the present invention, on the condition that at least one of the layers allows sufficient radiation to penetrate through the layer to enable the admixture to polymerize sufficiently. Accordingly, any cellulosic or polyolefin nonwoven web or film known in the art may be used as one of the layers so long as they allow radiation to pass through. Again, the amount of radiation sufficient to polymerize the admixture is readily determinable by one of ordinary skill in the art, and depends upon the identity and amount of photoinitiator, the identity and amount of the polymerizable material, the thickness of the admixture, the identity and thickness of the layer, the intensity and wavelength of the radiation, and the duration of exposure to the radiation.

The radiation to which the photoinitiators of the present invention may be exposed generally will have a wavelength of from about 4 to about 1,000 nanometers. Thus, the radiation may be ultraviolet radiation, including near ultraviolet and far or vacuum ultraviolet radiation; visible radiation; and near infrared radiation. Desirably, the radiation will have a wavelength of from about 100 to about 900 nanometers. More desirably, the radiation will have a wavelength of from about 100 to 700 nanometers. Desirably, the radiation will be ultraviolet radiation having a wavelength of from about 4 to about 400 nanometers. More desirably, the radiation will have a wavelength of from about 100 to about 420 nanometers, and even more desirably will have a wavelength of from 290 to about 320 nanometers. The radiation desirably will be incoherent, pulsed ultraviolet radiation from a dielectric barrier discharge excimer lamp or radiation from a mercury lamp.

Excimers are unstable excited-state molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. The dielectric barrier excimers in general emit in the range of from about 125 nm to about 500 nm, depending upon the excimer gas mixture.

Dielectric barrier discharge excimer lamps (also referred to hereinafter as "excimer lamp") are described, for example, by U. Kogelschatz, "Silent discharges for the generation of ultraviolet and vacuum ultraviolet excimer radiation." Pure & Appl. Chem., 62, No. 9, pp. 16671674 (1990); and E. Eliasson and U. Kogelschatz, "UV Excimer Radiation from Dielectric- Barrier Discharges." Appl. Phys. B. 46, pp. 299–303 (1988). Excimer lamps were developed by ABB Infocom Ltd., Lenzburg, Switzerland, and at the present time are available from Heraeus Noblelight GmbH, Kleinostheim, Germany.

The excimer lamp emits incoherent, pulsed ultraviolet radiation. Such radiation has a relatively narrow bandwidth, i.e., the half width is of the order of approximately 5 to 100 nanometers. Desirably, the radiation will have a half width of the order of approximately 5 to 50 nanometers, and more desirably will have a half width of the order of 5 to 25 nanometers. Most desirably, the half width will be of the order of approximately 5 to 15 nanometers.

The ultraviolet radiation emitted from an excimer lamp can be emitted in a plurality of wavelengths, wherein one or more of the wavelengths within the band are emitted at a maximum intensity. Accordingly, a plot of the wavelengths in the band against the intensity for each wavelength in the band produces a bell curve. The "half width" of the range of ultraviolet radiation emitted by an excimer lamp is defined as the width of the bell curve at 50% of the maximum height of the bell curve.

The emitted radiation of an excimer lamp is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification and the claims. Thus, in comparison with most other commercially useful sources of ultraviolet radiation which typically emit over the entire ultraviolet spectrum and even into the visible region, excimer lamp radiation is essentially monochromatic.

Although excimer lamps are highly desirable for use in the present invention, the source of radiation used with the photoinitiators of the present invention may be any radiation source known to those of ordinary skill in the art. In a further embodiment of the present invention, a mercury lamp with a D-bulb, which produces radiation having an emission peak of about 360 nm is used to produce free radicals from the above-described photoinitiators. This radiation source is particularly useful when matched with one or more photoinitiators of the present invention having an absorption maximum of about 360 nanometers, corresponding to the emission peak of the mercury lamp. Other specialty-doped lamps, which emit radiation at about 420 nm, may be used with photoinitiators of the present invention which have an absorption maximum at about 420 nm. One lamp, the V-bulb available from Fusion Systems, is another suitable lamp for use in the present invention. In addition, specialty lamps having a specific emission band may be manufactured for use with one or more specific photoinitiators of the present invention. New lamp technology provides the following potential advantages:

(a) substantially single wavelength output;
(b) unique wavelength output;
(c) high intensity; and
(d) absence of radiation trapping.

As a result of the photoinitiators of the present invention absorbing radiation in the range of about 250 to about 390 nm, some of the photoinitiators of the present invention will generate one or more reactive species upon exposure to sunlight. Accordingly, these photoinitiators of the present invention provide a method for the generation of reactive species that does not require the presence of a special light source.

The photoinitiators of the present invention enable the production of adhesive and coating compositions that consumers can apply to a desired object and polymerize or cure upon exposure to sunlight. These photoinitiators also enable numerous industry applications wherein polymerizable materials may be polymerized merely upon exposure to sunlight. Therefore, depending upon how the photoinitiator is designed, the photoinitiator of the present invention can eliminate the cost of purchasing and maintaining light sources in numerous industries wherein such light sources are necessary without the photoinitiators of the present invention.

The effective tuning of the photoinitiators of the present invention for a specific wavelength band permits the photoinitiators of the present invention to more efficiently utilize the target radiation in the emission spectrum of the radiating source corresponding to the "tuned" wavelength band, even though the intensity of such radiation may be much lower than, for example, radiation from a narrow band emitter, such as an excimer lamp. For example, it may be desirable to utilize an excimer lamp, or other radiation emission source, that emits radiation having a wavelength of approximately 360 nm or 420 nm with the photoinitiators of the present invention. However, the effectiveness of the photoinitiators of the present invention is not necessarily dependent upon the availability or use of a narrow wavelength band radiation source.

Use of the Above-Described Photoinitiators in an Ink Composition

The above-described photoinitiators of the present invention may be incorporated into ink compositions. In one embodiment of the present invention, one or more of the photoinitiators are incorporated into an ink jet ink composition for use on ink jet ink printers. The ink composition may be used on commercially available ink jet printing machines alone or in combination with a radiation source in series with the ink jet printing machine for instantaneous curing of the ink jet ink composition. Any radiation source known to those of ordinary skill in the art may be used to cure the ink jet ink composition. Desirably, one of the above-described radiation sources is used to cure the ink composition.

Use of the Above-Described Photoinitiators in Other Radiation-Drying Printing Process A further use of the above-described photoinitiators of the present invention involves the incorporation of one or more of the photoinitiators into an ink composition for use on a radiation-drying printing press. As discussed above, "radiation-drying printing" refers to any printing method which utilizes radiation as a drying means. Radiation-drying printing includes, for example, offset printing operations, such as on a Heidelberg press, flexographic printing, and flatbed printing.

The photoinitiators of the present invention enable increased press output due to the photoreactivity of the photoinitiators. Further, the increased output may be obtained while using a minimal amount of photoinitiator and a low energy light source. In one embodiment of the present invention, complete curing at an output rate of 10,000 printed sheets per hour may be obtained using a 50 W cold lamp as the light source.

Any of the above-described photoinitiators may be used in the printing processes disclosed herein. Desirably, the amount of photoinitiator added to the ink composition, adhesive composition or resin is less than about 4.0 wt % of the total weight of the composition. More desirably, the amount of photoinitiator added to the composition is from about 0.25 to about 3.0 wt % of the total weight of the composition. Most desirably, the amount of photoinitiator added to the composition is from about 0.25 to about 2.0 wt % of the total weight of the composition.

A major advantage of the photoinitiators of the present invention is that they enable rapid curing times of ink compositions, adhesive compositions and/or resins in comparison to the curing times of prior art photoinitiators. The use of the photoinitiators of the present invention in ink compositions, adhesive compositions or resins for printing presses enables print speeds, which were at one time thought to be unobtainable. For example, in an open air printing process using a Heidelberg print press and a 50 W excimer cold lamp for photocuring, desirably the printed sheet output is greater than 6,000 sheets per hour. More desirably, the printed sheet output is greater than 8,000 sheets per hour. Most desirably, the printed sheet output is greater than 10,000 sheets per hour.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A photoinitiator having the general formula:

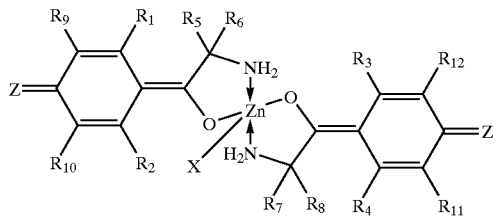

wherein Z each independently represents

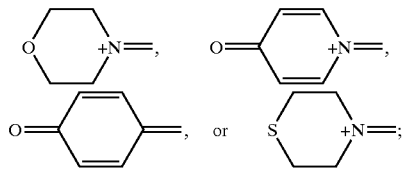

wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$ and $R_{12}$ comprise an alkyl group, an aryl group, a halo group, an alkoxy group or hydrogen and wherein at least one of $R_9$, $R_{10}$, $R_{11}$ and $R_{12}$ comprises an alkyl, an aryl, a halo, or an alkoxy group.

2. The photoinitiator of claim 1, wherein at least $R_9$ or $R_{10}$ and at least $R_{11}$ or $R_{12}$ comprise an alkyl, an aryl, a halo, or an alkoxy group.

3. The photoinitiator of claim 2, wherein $R_1$, $R_2$, $R_3$ and $R_4$ are hydrogen; X is $H_2O$; and Z is

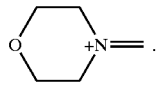

4. The photoinitiator of claim 3, wherein $R_5$, $R_6$, $R_7$ and $R_8$ are $CH_3$.

5. The photoinitiator of claim 4, wherein the photoinitiator is associated with a counterion, the counterion comprising tetrafluoroboron.

6. The photoinitiator of claim 3, wherein $R_6$ and $R_7$ comprise an aryl group.

7. The photoinitiator of claim 3, wherein $R_5$, $R_6$, $R_7$ and $R_8$ are $Ph(CH_2)_2$.

8. The photoinitiator of claim 2, wherein the photoinitiator is associated with one or more counterions.

9. The photoinitiator of claim 8, wherein the one or more counterions comprise tetraphenylboron, tetrachloroboron, tetrafluoroboron, hexafluorophosphate, perchlorate, or a combination thereof.

10. The photoinitiator of claim 9, wherein the one or more counterions comprise tetraphenylboron or tetrafluoroboron.

11. A method of generating a reactive species, comprising: irradiating the photoinitiator of claim 2 with radiation.

12. A method of polymerizing a polymerizable material, comprising:
irradiating an admixture of a polymerizable material and the photoinitiator of claim 2.

13. The photoinitiator of claim 1, wherein Z comprises

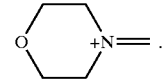

14. A photoreactive composition comprising at least one photoinitiator and at least one counterion, wherein the composition is capable of generating at least one cationic free radical and at least one nitrogen radical species, wherein the photoinitiator has the general formula:

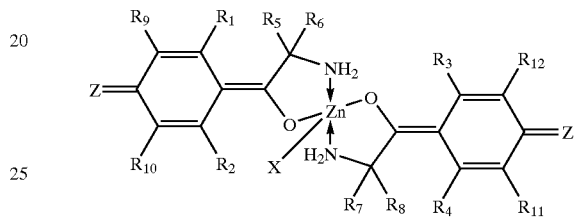

wherein Z each independently represents

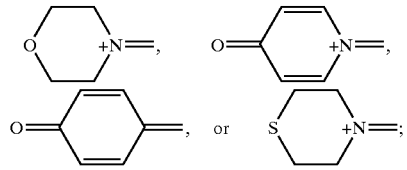

wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$ and $R_{12}$ comprise an alkyl group, an aryl group, a halo group, an alkoxy group or hydrogen and wherein at least one of $R_9$, $R_{10}$, $R_{11}$ and $R_{12}$ comprises an alkyl, an aryl, a halo, or an alkoxy group.

15. The photoreactive composition of claim 14, wherein at least $R_9$ or $R_{10}$ and $R_{11}$ or $R_{12}$ comprise an alkyl, an aryl, a halo, or an alkoxy group.

16. The photoreactive composition of claim 15, wherein $R_1$, $R_2$, $R_3$ and $R_4$ are hydrogen; X is $H_2O$; and Z is

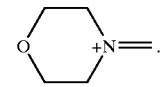

17. The photoreactive composition of claim 16, wherein $R_5$, $R_6$, $R_7$ and $R_8$ are $CH_3$.

18. The photoreactive composition of claim 17, wherein the counterion comprises tetrafluoroboron.

19. The photoreactive composition of claim 16, wherein $R_6$ and $R_7$ comprise an aryl group.

20. The photoreactive composition claim 16, wherein $R_5$, $R_6$, $R_7$ and $R_8$ are $Ph(CH_2)_2$.

21. The photoreactive composition of claim 15, wherein Z comprises

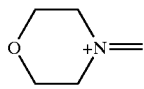

22. The photoreactive composition of claim 15, wherein the at least one counterion comprises tetraphenylboron, tetrachloroboron, tetrafluoroboron, hexafluorophosphate, perchlorate, or a combination thereof.

23. A photoinitiator having the general formula:

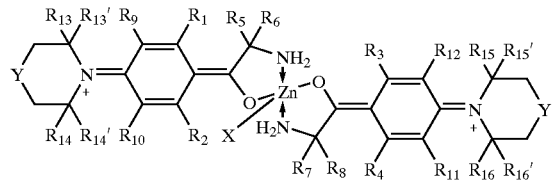

wherein Y independently represents O, S, or O=C; wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$, $R_{12}$, $R_{13}$, $R_{13}'$, $R_{14}$, $R_{14}'$, $R_{15}$, $R_{15}'$, $R_{16}$, and $R_{16}'$ comprise an alkyl group, an aryl group, a halo group, an alkoxy group, or hydrogen; $R_{13}'$ $R_{14}'$ $R_{15}'$ and $R_{16}'$ being the same or different from $R_{13}$, $R_{14}$, $R_{15}$ and $R_{16}'$; and wherein at least one of $R_{13}$, $R_{14}$, $R_{15}$ and $R_{16}$ comprises an alkyl, an aryl, a halo, or an alkoxy group.

24. The photoinitiator of claim 23, wherein at least one of $R_{13}$ or $R_{14}$ and at least one of $R_{15}$ or $R_{16}$ comprises an alkyl, an aryl, a halo, or an alkoxy group.

25. The photoinitiator of claim 24, wherein at least one of $R_9$ or $R_{10}$ and at least one of $R_{11}$ or $R_{12}$ comprises an alkyl, an aryl, a halo, or an alkoxy group.

26. The photoinitiator of claim 25; wherein Y comprises O.

27. The photoinitiator of claim 26, wherein $R_1$, $R_2$, $R_3$ and $R_4$ are hydrogen and X is $H_2O$.

28. The photoinitiator of claim 27, wherein $R_5$, $R_6$, $R_7$ and $R_8$ are $CH_3$.

29. The photoinitiator of claim 27, wherein $R_6$ and $R_7$ comprise aryl groups.

30. The photoinitiator of claim 27, wherein $R_5$, $R_6$, $R_7$ and $R_8$ comprise $Ph(CH_2)_2$.

31. The photoinitiator of claim 25, wherein the photoinitiator is associated with one or more counterions.

32. The photoinitiator of claim 31, wherein the one or more counterions comprise tetraphenylboron, tetrachloroboron, tetrafluoroboron, hexafluorophosphate, perchlorate, or a combination thereof.

33. The photoinitiator of claim 31, wherein the one or more counterions comprise tetraphenylboron or tetrafluoroboron.

34. A method of generating a reactive species, comprising: irradiating the photoinitiator of claim 25 with radiation.

35. A method of polymerizing a polymerizable material, comprising:

irradiating an admixture of a polymerizable material and the photoinitiator of claim 25.

36. A photoreactive composition comprising at least one photoinitiator and at least one counterion, wherein the composition is capable of generating at least one cationic free radical and at least one nitrogen radical species, the photoinitiator having the general formula:

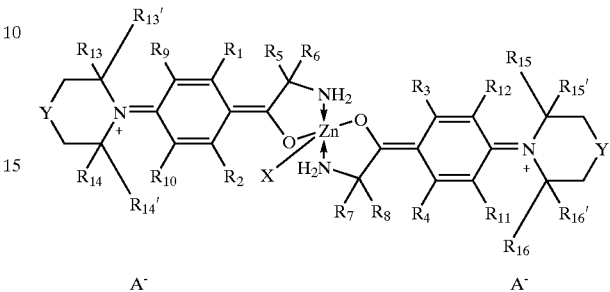

wherein Y independently represents O, S, or O=C; wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$, $R_{12}$, $R_{13}$, $R_{13}'$, $R_{14}$, $R_{14}'$, $R_{15}$, $R_{15}'$, $R_{16}$, and $R_{16}'$ comprise an alkyl group, an aryl group, a halo group, an alkoxy group, or hydrogen; $R_{13}'$ $R_{14}'$ $R_{15}'$ and $R_{16}'$ being the same or different from $R_{13}$, $R_{14}$, $R_{15}$ and $R_{16}'$ wherein at least one of $R_{13}$, $R_{14}$, $R_{15}$ and $R_{16}$ comprises an alkyl, an aryl, a halo, or an alkoxy group; and $A^-$ comprises a counterion.

37. The photoreactive composition of claim 36, wherein at least one of $R_{13}$ or $R_{14}$ and at least one of $R_{15}$ or $R_{16}$ comprises an alkyl, an aryl, a halo, or an alkoxy group.

38. The photoreactive composition of claim 37, wherein at least one of $R_9$ or $R_{10}$ and at least one of $R_{11}$ or $R_{12}$ comprises an alkyl, an aryl, a halo, or an alkoxy group.

39. The photoreactive composition of claim 38, wherein Y comprises O.

40. The photoreactive composition of claim 39, wherein $R_1$, $R_2$, $R_3$ and $R_4$ are hydrogen and X is $H_2O$.

41. The photoreactive composition of claim 40, wherein $R_5$, $R_6$, $R_7$ and $R_8$ are $CH_3$.

42. The photoreactive composition of claim 40, wherein $R_6$ and $R_7$ comprise aryl groups.

43. The photoreactive composition of claim 40, wherein $R_5$, $R_6$, $R_7$ and $R_8$ comprise $Ph(CH_2)_2$.

44. The photoreactive composition of claim 38, wherein the at least one counterion comprises tetraphenylboron, tetrachloroboron, tetrafluoroboron, hexafluorophosphate, perchlorate, or a combination thereof.

45. A method of generating a reactive species, comprising:

irradiating a photoinitiator with radiation, wherein at least one cationic free radical and at least one nitrogen radical species are generated, wherein the photoinitiator has the general formula:

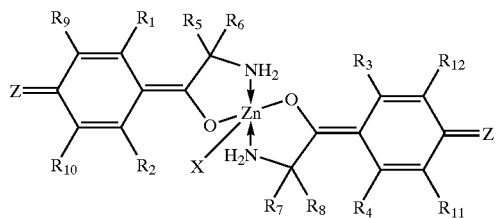

wherein Z each independently represents

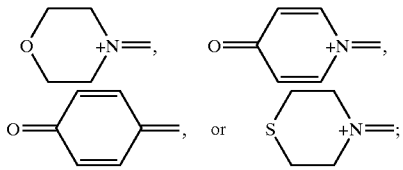

wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$ and $R_{12}$ comprise an alkyl group, an aryl group, a halo group, an alkoxy group or hydrogen and wherein at least one of $R_9$, $R_{10}$, $R_{11}$ and $R_{12}$ comprises an alkyl, an aryl, a halo, or an alkoxy group.

46. The method of claim 45, wherein at least $R_9$ or $R_{10}$ and at least $R_{11}$ or $R_{12}$ comprise an alkyl, an aryl, a halo, or an alkoxy group.

47. The method of claim 46, wherein $R_1$, $R_2$, $R_3$ and $R_4$ are hydrogen; X is $H_2O$; and Z is

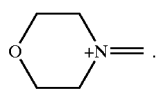

48. The method of claim 47, wherein $R_5$, $R_6$, $R_7$ and $R_8$ are $CH_3$.

49. The method of claim 47, wherein $R_6$ and $R_7$ comprise an aryl group.

50. The method of claim 47, wherein $R_5$, $R_6$, $R_7$ and $R_8$ are $Ph(CH_2)_2$.

51. The method of claim 46, wherein the photoinitiator is associated with one or more counterions.

52. The method of claim 51, wherein the one or more counterions comprise tetraphenylboron, tetrachloroboron, tetrafluoroboron, hexafluorophosphate, perchlorate, or a combination thereof.

53. The method of claim 52, wherein the one or more counterions comprise tetraphenylboron or tetrafluoroboron.

54. The method of claim 46, wherein the photoinitiator is associated with a counterion, the counterion comprising tetrafluoroboron.

55. The method of claim 46, wherein Z comprises

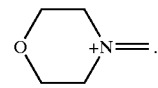

56. A method of generating a reactive species comprising:
irradiating a photoinitiator with radiation, wherein at least one cationic free radical and at least one nitrogen radical species are generated, wherein the photoinitiator has the general formula:

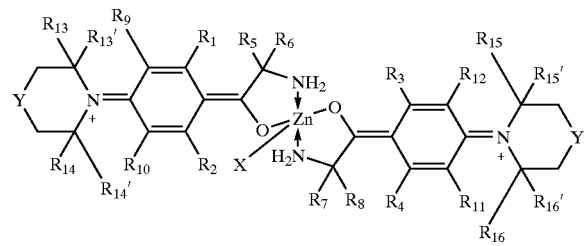

wherein Y independently represents O, S, or O=C; wherein $R_1$, $R_2$, $R_3$ and $R_4$ each independently represent hydrogen, an alkyl group having from one to six carbon atoms, an alkoxy group having from one to six carbon atoms, or a halogen-substituted alkyl group; $R_5$, $R_6$, $R_7$ and $R_8$ each independently represent an alkyl group having from one to six carbon atoms, an aryl group, or a halogen-substituted alkyl group having from one to six carbon atoms; wherein X represents $(R_{17})_2O$ or $(R_{17})_3N$, wherein $R_{17}$ represents H or an alkyl group having from one to eight carbon atoms; and wherein $R_9$, $R_{10}$, $R_{11}$, $R_{12}$, $R_{13}$, $R_{13}'$, $R_{14}$, $R_{14}'$, $R_{15}$, $R_{15}'$, $R_{16}$, and $R_{16}'$ comprise an alkyl group, an aryl group, a halo group, an alkoxy group, or hydrogen; $R_{13}'$ $R_{14}'$ $R_{15}'$ and $R_{16}'$ being the same or different from $R_{13}$, $R_{14}$, $R_{15}$ and $R_{16}'$; and wherein at least one of $R_{13}$, $R_{14}$, $R_{15}$ and $R_{16}$ comprises an alkyl, an aryl, a halo, or an alkoxy group.

57. The method of claim 56, wherein at least one of $R_{13}$ or $R_{14}$ and at least one of $R_{15}$ or $R_{16}$ comprises an alkyl, an aryl, a halo, or an alkoxy group.

58. The method of claim 57, wherein at least one of $R_9$ or $R_{10}$ and at least one of $R_{11}$ or $R_{12}$ comprises an alkyl, an aryl, a halo, or an alkoxy group.

59. The method of claim 58, wherein Y comprises O.

60. The method of claim 59, wherein $R_1$, $R_2$, $R_3$ and $R_4$ are hydrogen and X is $H_2O$.

61. The method of claim 60, wherein $R_5$, $R_6$, $R_7$ and $R_8$ are $CH_3$.

62. The method of claim 60, wherein $R_6$ and $R_7$ comprise aryl groups.

63. The method of claim 60, wherein $R_5$, $R_6$, $R_7$ and $R_8$ comprise $Ph(CH_2)_2$.

64. The method of claim 58, wherein the photoinitiator is associated with one or more counterions.

65. The method of claim 64, wherein the one or more counterions comprise tetraphenylboron, tetrachloroboron, tetrafluoroboron, hexafluorophosphate, perchlorate, or a combination thereof.

66. The method of claim 64, wherein the one or more counterions comprise tetraphenylboron or tetrafluoroboron.

* * * * *

UNITED STATES PATENT AND TRADEMARK OFFICE
CERTIFICATE OF CORRECTION

PATENT NO. : 6,780,896 B2
DATED : August 24, 2004
INVENTOR(S) : John Gavin MacDonald and Jason Lye It is certified that error appears in the above-identified patent and that said Letters Patent is hereby corrected as shown below:

Title page,
Item [56], References Cited, U.S. PATENT DOCUMENTS, the following should be added:
-- 4,701,218   10/1997     Barker, et al.
5,221,332     6/1993      Kohlmeier
5,344,874     9/1994      Debord, et al. --
Please change "6,156,649     12/2000     Hause, et al." to -- 6,159,649     12/2000     Macholdt, et al. --
FOREIGN PATENT DOCUMENTS, the following should be added:
-- DE   2052198       10/1970 --

Signed and Sealed this

Fourteenth Day of June, 2005

JON W. DUDAS
*Director of the United States Patent and Trademark Office*